(12) United States Patent
Stochniol et al.

(10) Patent No.: US 10,221,110 B2
(45) Date of Patent: Mar. 5, 2019

(54) DEHYDROGENATION OF OLEFIN-RICH HYDROCARBON MIXTURES

(71) Applicant: EVONIK DEGUSSA GMBH, Essen (DE)

(72) Inventors: Guido Stochniol, Haltern am See (DE); Robert Franke, Marl (DE)

(73) Assignee: EVONIK DEGUSSA GMBH, Essen (DE)

( * ) Notice: Subject to any disclaimer, the term of this patent is extended or adjusted under 35 U.S.C. 154(b) by 0 days.

(21) Appl. No.: 15/827,193

(22) Filed: Nov. 30, 2017

(65) Prior Publication Data

US 2018/0162791 A1 Jun. 14, 2018

(30) Foreign Application Priority Data

Dec. 8, 2016 (EP) ..................... 16202840

(51) Int. Cl.
*C07C 5/333* (2006.01)
*C07C 5/52* (2006.01)
*C07C 11/02* (2006.01)
*C10G 35/085* (2006.01)

(52) U.S. Cl.
CPC ............ *C07C 5/3337* (2013.01); *C07C 5/333* (2013.01); *C07C 5/52* (2013.01); *C07C 11/02* (2013.01); *C10G 35/085* (2013.01); *C10G 2300/1081* (2013.01); *C10G 2300/1088* (2013.01)

(58) Field of Classification Search
None
See application file for complete search history.

(56) References Cited

U.S. PATENT DOCUMENTS

| 4,013,733 A | 3/1977 | Rausch |
| 4,152,365 A | 5/1979 | Drehman |
| 4,926,005 A | 5/1990 | Olbrich et al. |

(Continued)

FOREIGN PATENT DOCUMENTS

| DE | 10229661 A1 | 4/2003 |
| EP | 3293171 A1 | 3/2018 |

OTHER PUBLICATIONS

U.S. Appl. No. 15/689,322, filed Aug. 29, 2017.

(Continued)

*Primary Examiner* — Philip Y Louie
(74) *Attorney, Agent, or Firm* — Smith, Gambrell & Russell, LLP

(57) ABSTRACT

A process for dehydrating alkanes in which such feedstock mixtures may be used having a high proportion of olefins, i.e. approximately 1% by weight to 10% by weight. Specifically, alkenes having two to five carbon atoms are generated from alkanes having the same carbon length where the number of carbon atoms not change during by the dehydrogenation. The process is intended to be feasible on an industrial scale. A basic concept of the invention consists of hydrogenating alkenes present in the feedstock to the corresponding alkanes before they come in contact with the dehydrogenation catalyst. This avoids an undesired coke deposit. The hydrogenation is effected by minimal addition of hydrogen (80% to 120% of the stoichiometrically required amount). The hydrogenation is effected either over a dehydrogenation catalyst, or over the dehydrogenation catalyst itself.

13 Claims, 1 Drawing Sheet

(56) References Cited

U.S. PATENT DOCUMENTS

| | | | |
|---|---|---|---|
| 5,008,414 A * | 4/1991 | Ramachandran | C07C 253/26 |
| | | | 549/523 |
| 5,151,401 A | 9/1992 | Schubert et al. | |
| 5,389,342 A | 2/1995 | Savage et al. | |
| 6,187,985 B1 * | 2/2001 | Le Peltier | B01J 23/622 |
| | | | 585/442 |
| 2006/0122436 A1 | 6/2006 | Schindler et al. | |
| 2016/0326069 A1 * | 11/2016 | Suriye | B01J 21/10 |
| 2018/0072647 A1 | 3/2018 | Stochniol et al. | |

OTHER PUBLICATIONS

Geilen, F. M., et al. Ullmann's Encyclopedia of Industrial Chemistry: Butenes. 2013. pp. 1-13.

Schweitzer et al. Propylene Hydrogenation and Propane Dehydrogenation by a Single-Site $Zn^{2+}$ on Silica Catalyst. ACS Catalysis. 2014, vol. 4., pp. 1091-1098.

Non-published EP Priority Application 16188267.5 filed on Sep. 16, 2012.

European Search Report dated Apr. 5, 2018 for EP Patent Application No. 17204866 (4 pages).

* cited by examiner

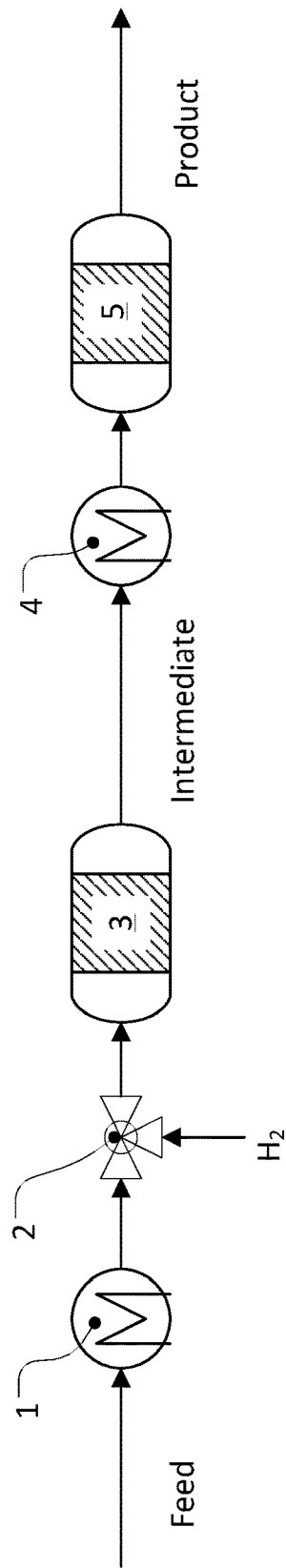

DEHYDROGENATION OF OLEFIN-RICH HYDROCARBON MIXTURES

The invention deals with the question of how mixtures of alkanes having two to five carbon atoms may be dehydrogenated if the mixture comprises a high proportion of olefins.

Hydrocarbons are chemical compounds which consist exclusively of carbon and hydrogen. Alkenes (synonym: olefins) are hydrocarbons which have a C=C double bond in the molecule. Alkanes (synonym: paraffins), on the other hand, are hydrocarbons which have only single bonds. They are therefore also referred to as saturated. Due to the different bond types, alkenes are significantly more reactive than alkanes. Therefore, alkenes are chemically more utilizable and correspondingly more valuable than alkanes.

In organic chemistry, hydrocarbons are frequently designated according to the number of carbon atoms which they have per molecule, in that the respective class of substances is preceded by the prefix $C_n$. "n" is the respective number of carbon atoms in a molecule. Thus, $C_4$ olefins are substances from the class of alkenes having four carbon atoms. $C_8$ olefins correspondingly have eight carbon atoms per molecule. Where the prefix $C_{n+}$ is used hereinafter, it refers to a class of substances which have more than n carbon atoms per molecule. A $C_{4+}$ olefin accordingly has at least five carbon atoms.#

Due to the different arrangement and linking possibilities of the carbon and hydrogen atoms, several isomers, which have the same number of carbon atoms, exist within the substance classes discussed here. For instance, two alkanes exist having four carbon atoms in each case, namely n-butane and isobutane. Since the variety of combinations is greater for the alkenes, even more isomers are possible. For instance, in total four olefins having four carbon atoms exist, namely isobutene, 1-butene, cis-2-butene and trans-2-butene. The three linear butenes, 1-butene, cis-2-butene and trans-2-butene, are often referred to collectively as n-butene. For the $C_3$-hydrocarbons in contrast, there is only one isomer in each case, namely the alkane having three carbon atoms, propane, and the $C_3$-alkene propene. In the longer-chain $C_{5+}$ hydrocarbons, the multiplicity of isomers increases markedly. Despite the identical number of carbon atoms, isomers have different properties which are relevant for their industrial use.

$C_4$-chemistry is concerned with the production of specialty chemicals from butenes. For an introduction see:

Geilen, F. M., Stochniol, G., Peitz, S. and Schulte-Koerne, E.: Butenes. Ullmann's Encyclopedia of Industrial Chemistry. 1-13. Published Online: 31 Jan. 2014 DOI: 10.1002/14356007.a04_483.pub3

As raw material source, so-called $C_4$-cuts are currently usually used which originate as "crack $C_4$" from steam-crackers or as "FCC-C4" from fluidized-catalytic crackers. Such crackers are substantially charged with naphtha or VGO (vacuum gas oil) which originate in turn from the distillation of crude oil. Since crack C4 and FCC-C4 are in the added-value chain of the petrochemical products of crack processes, the prices for these raw materials are correspondingly volatile owing to their dependence on the price of crude oil. Moreover, the availability of high-value crack C4 has been steadily falling since the operation of the steam cracker is optimized towards the production of the $C_2$- and $C_3$-olefins ethene and propene to the detriment of the $C_4$ yield.

Therefore, there is a fundamental interest in $C_4$ chemistry to render alternative raw materials usable in place of classical raw material sources.

Dehydrogenation technology offers one possibility here. Dehydrogenation is a chemical reaction in which hydrogen is removed from a hydrocarbon. Specifically, alkenes may be produced from alkanes with liberation of hydrogen ($H_2$). The number of carbon atoms of the alkenes generated then corresponds to that of the alkanes used. Since alkanes are less reactive than alkenes, energy has to be expended for the dehydrogenation. This can be supplied to the reaction in the form of heat. In the interest of energy savings, industrial dehydrogenation is always carried out in the presence of solid catalysts.

The technology for dehydrogenating alkanes is differentiated into oxidative processes and non-oxidative processes. In oxidative dehydrogenation, an oxidizing agent such as oxygen or air is supplied to the alkane mixture in order to assure the heat requirement of the strongly endothermic dehydrogenation at least partially by the oxidation of the liberated hydrogen. In non-oxidative dehydrogenation, however, the addition of oxidizing agents is omitted and instead the heat required is introduced into the reactor externally, for example by heating with a fuel gas (usually methane, natural gas, cracking gases from the dehydration process and optionally partly admixing hydrogen formed in the dehydrogenation). Both process variants differ significantly in the composition of the dehydrogenation mixture. A detailed discourse on common dehydrogenation technology can be found in US2006/0122436A1.

A problem in industrially practised dehydrogenation is coke formation on the catalyst. What is meant by this is a precipitate of carbon on the surface of the catalyst. This leads to a deactivation of the catalyst, such that this must be exchanged or regenerated. The operating costs increase greatly thereby such that the dehydrogenation is uneconomical.

For this reason, the presence of alkenes in the inlet region of the dehydrogenation catalyst is undesirable since, due to their higher reactivity compared to alkanes, they lead to a rapid coke deposition on the catalyst. Consequently, providers of commercial dehydrogenation processes advise against introducing alkenes into the dehydrogenation.

If large amounts of olefins are present in the feedstock mixture to be dehydrogenated, appropriate measures have to be taken in order to counter coking:

For instance, U.S. Pat. No. 5,389,342 describes the apparatus setup of a reactor for dehydrogenating n-butane and isobutane. A liquid feedstock mixture with the alkanes to be dehydrogenated is transferred to an evaporator in the gas phase and then diluted with steam in order to reduce coke deposits during the contact with the dehydrogenation catalyst and to increase the conversion.

The addition of steam uses the effect of carbon gasification after the carbon is converted into synthesis gas in the presence of steam:

$$C + H_2O \rightarrow CO + H_2$$

A disadvantage is that the reactive synthesis gas forms many undesirable by-products which only have to be laboriously removed again from the product mixture of the dehydrogenation.

U.S. Pat. No. 4,926,005 describes a method in which a $C_2$ to $C_5$ paraffin mixture, prior to a non-oxidative dehydrogenation, is contacted with a used dehydrogenation catalyst under non-dehydrogenating conditions in order to increase the alkane conversion. The precontact takes place at temperatures between 0° C. and 120° C. and in the absence of hydrogen and oxygen. Potentially, S or N components are absorbed therein. Olefins in the inlet are not mentioned.

U.S. Pat. No. 4,013,733 describes a $C_4$ to $C_{30}$ paraffin mixture which, prior to contact with the dehydrogenation catalyst, is treated with hydrogen. During contact, temperatures are between 371° C. and 677° C. The ratio of hydrogen to hydrocarbon is from 1:1 to 20:1. The hydrogen is injected directly into the dehydrogenation zone. The purpose of the hydrogen addition is to produce those target substances having the same number of carbon atoms as the starting materials but having a reduced number of hydrogen atoms. Olefins are not present in the feedstock mixture.

The group of Neil M Schweitzer also discusses the problem of catalyst deactivation caused by carbon deposits. A catalyst system is described based on zinc and silica which is suitable both for hydrogenation of propene and for dehydrogenation of propane:

Schweitzer et al.: Propylene Hydrogenation and Propane Dehydrogenation by a Single-Site Zn2+ on Silica Catalyst. ACS Catal., 2014, 4 (4), pp 1091-1098. DOI: 10.1021/cs401116p The hydrogenation was effected at 200° C. and the dehydrogenation at 550° C. or at 650° C. A disadvantage is the large hydrogen excess (molar ratio of hydrogen:propene is ca. 10:1) with which it is carried out here, since such a large excess may negatively influence the hydrogenation↔dehydrogenation equilibrium reaction, wherein the dehydrogenation in particular would proceed very unfavourably. For this reason, the hydrogenation and dehydrogenation are not carried out consecutively as is the case here but rather are investigated independently of each other. A further disadvantage is [MTR1] that zinc is not an effective hydrogenation component for hydrogenating olefins, which is suitable for unrestricted use on an industrial scale.

The European patent application 16188267.5, which was yet to be published at the filing date, is concerned with the dehydrogenation of liquified petroleum gas (LPG). Prior to the dehydrogenation, a hydrogenation is optionally provided in order to decrease the olefin content of the LPG to a value below 1% by weight. The hydrogenation takes place in the liquid phase.

With regard to this prior art, the object of the invention is to specify a process for dehydrogenating alkanes in which such feedstock mixtures may be used having a high proportion of olefins, i.e. approximately 1% by weight to 10% by weight. Specifically, alkenes having two to five carbon atoms should be generated from alkanes having the same chain length and therefore the number of carbon atoms should not be changed by the dehydrogenation. The process is intended to be feasible on an industrial scale.

The object is achieved by a process having the following steps:
a) providing a liquid feedstock mixture at a pressure between $0.1*10^5$ Pa and $6.0*10^5$ Pa, wherein the feedstock mixture comprises alkanes having two to five carbon atoms and alkenes having two to five carbon atoms, and wherein the part by mass of alkenes in the feedstock mixture based on the total mass thereof is 1% by weight to 10% by weight;
b) evaporating the feedstock mixture by increasing the temperature;
c) adding hydrogen to the evaporated feedstock mixture such that the molar ratio of hydrogen to the alkenes present in the feedstock mixture is between 0.8:1 and 1.2:1;
d1) contacting the evaporated, hydrogen-containing feedstock mixture with a solid catalyst at a temperature between 450° C. and 760° C. and a pressure of $0.1*10^5$ Pa to $6.0*10^5$ Pa to obtain a product mixture, wherein the part by mass of the alkenes having two to five carbon atoms in the product mixture based on the total mass thereof is 30% by weight to 70% by weight; or
d2) contacting the evaporated, hydrogen-containing feedstock mixture with a first solid catalyst and a pressure between $0.1*10^5$ Pa and $6*10^5$ Pa to obtain an intermediate, wherein the part by mass of the alkenes in the intermediate based on the total mass thereof is 0% by weight to 1% by weight and wherein the temperature of the evaporated, hydrogen-containing feedstock mixture and/or of the intermediate is increased; and
e) contacting the intermediate with a second solid catalyst at a temperature between 450° C. and 760° C. and a pressure of $0.1*10^5$ Pa to $6.0*10^5$ Pa to obtain a product mixture, wherein the part by mass of the alkenes having two to five carbon atoms in the product mixture based on the total mass thereof is 30% by weight to 70% by weight.

The subject matter of the invention relates to such a process.

A basic concept of the invention consists of hydrogenating alkenes present in the feedstock mixture to the corresponding alkanes before they come into contact with the dehydrogenation catalyst. An undesired coke deposit is thus avoided. The hydrogenation is effected by minimal addition of hydrogen (80% to 120% of the stoichiometrically required amount). The hydrogenation is effected either over a hydrogenation catalyst specifically provided therefor, which differs from the dehydrogenation catalyst, or over the dehydrogenation catalyst itself.

An important aspect of the invention consists in that the hydrogenation (on contact with the first catalyst) is effected in the gas phase. For this purpose, the liquid feedstock mixture is firstly evaporated and then hydrogen is metered in prior to the hydrogenation.

The addition of hydrogen to the gaseous (evaporated) feedstock mixture has the advantage that solubility limits of hydrogen are irrelevant: due to the occasionally high proportion of olefin in the feedstock mixture, a large amount of hydrogen is also required for complete hydrogenation. If the hydrogenation is to be carried out in the liquid phase, the hydrogen would have to be dissolved in the liquid feedstock mixture, wherein corresponding solubility limits would be relevant. It would not be possible to completely hydrogenate a highly olefinic feedstock mixture in the liquid phase, if at all, since the amount of hydrogen required for the hydrogenation could not be dissolved in the liquid phase. Consequently, this would result in coke deposits in the downstream dehydrogenation due to non-hydrogenated olefin.

A further important aspect of the invention is that the hydrogenation is effected at the same pressure level as the dehydrogenation, i.e. between $0.1*10^5$ Pa and $6.0*10^5$ Pa. The entire process is preferably carried out isobarically, i.e. the feedstock mixture is already provided at reaction pressure (of the dehydrogenation) and then this pressure is also maintained during the evaporation and the hydrogenation.

The reason for this is that the hydrogenation at these high pressures constitutes the equilibrium reaction of the dehydrogenation. The hydrogenation is favoured at low temperatures and the dehydrogenation at high temperatures. Consequently, in the process according to the invention, the temperature is increased during the course of the hydrogenation such that only after the hydrogenation is the high dehydrogenation temperature applied which favours the dehydrogenation over the second catalyst.

The use of the dehydrogenation catalyst for hydrogenating olefins is thus based on the understanding that the hydrogenation and dehydrogenation are equilibrium reactions which can be influenced thermodynamically in a desired direction. Specifically, mild temperatures (20° C. to 220° C.) favour the hydrogenation whereas at higher temperatures (450° C. to 760° C.) the dehydrogenation dominates. Accordingly, the thermodynamic conditions in the first contact (for the hydrogenation) and in the second contact (for the dehydrogenation) are adjusted in accordance with the invention so that the equilibrium is shifted in the desired direction.

More precisely, the adjustment of the thermodynamic conditions consists of increasing the temperature. This is accomplished by either heating the intermediate (i.e. the hydrogenated feed mixture) and/or by heating the feed mixture already in contact with the first catalyst. It should be noted here that the hydrogenation is exothermic and in this respect the heat of reaction of the hydrogenation released can also be used to preheat the resulting intermediate. Means of heating the intermediate or the hydrogen-containing feedstock mixture are therefore not strictly required. The dehydrogenation temperature (between 450° C. and 760° C.) may not be achieved in the presence of the first catalyst however, since the first catalyst then effects dehydrogenation and would be rapidly covered with coke.

In a fundamental variant of the invention, the first catalyst and the second catalyst are identical. This means that the same solid catalyst is used in the hydrogenation and in the dehydrogenation. This lowers the catalyst costs of the process since only one catalytically active substance has to be handled for both process steps. This assumes that the catalyst catalyzes both the hydrogenation (and at elevated temperature) the dehydrogenation.

For this purpose, suitable supported catalysts are in principle those which have a support material and a hydrogenation-active component applied thereto. Suitable hydrogenation-active components are those elements which are listed in groups 8, 9 and 10 of the Periodic Table of the Elements according to IUPAC convention. The elements tin and zinc are particularly suitable. The (first and second) solid catalyst particularly preferably have a support material and at least tin and/or zinc. In addition to or instead of tin and/or zinc, further hydrogenation-active components may also be present, such as, for example, nickel, platinum or palladium.

Optionally, silicon dioxide or aluminium oxide are suitable as support material. It is also possible to use a chemical or physical mixture of silicon dioxide and aluminium oxide as support material. Chemical mixtures of silicon dioxide and aluminium oxide are often referred to as silica/alumina. It is possible to use both amorphous silica/alumina and crystalline (so-called zeolites) as support material. Suitable support materials are also aluminates which are formed from aluminium oxide and an alkaline earth metal such as calcium. Hydrotalcite is also otherwise suitable as support material for a combined hydrogenation/dehydrogenation catalyst.

A particularly suitable tin/zinc system as first and second catalyst on calcium-modified aluminium oxide or preparation thereof and use in dehydrogenation is disclosed in U.S. Pat. No. 4,152,365, U.S. Pat. No. 4,926,005 and U.S. Pat. No. 5,151,401. This catalyst also comprises platinum.

A second fundamental variant of the invention provides that different catalysts are used for the hydrogenation and for the dehydrogenation. Accordingly, the first and second solid catalyst are not identical. An advantage of this is that the catalysts can be optimized for their respective task.

The first solid catalyst used is preferably a supported catalyst which comprises a support material and at least one element applied thereto selected from the group consisting of nickel, platinum and palladium, i.e. a catalyst which may influence the hydrogenation particularly advantageously [MTR2].

Suitable support materials are in turn silicon dioxide or aluminium oxide or a physical or chemical mixture thereof; as well with regards as to the combined catalysts listed above. Suitable as second catalyst is a system such as described above as first and second catalyst.

The process is intended for the purpose of processing feedstock mixtures having the following specification:
Propane: 0% by weight to 50% by weight;
Isobutane: 0% by weight to 100% by weight;
n-Butane: 0% by weight to 100% by weight;
Propene: 0% by weight to 10% by weight;
Isobutene: 0% by weight to 10% by weight;
n-Butene: 0% by weight to 10% by weight;
sum of other substances: 0% by weight to 5% by weight.

Therefore, it takes the form essentially of a mixture of $C_3$ and/or $C_4$ hydrocarbons.

The components present add up to 100% by weight. All components specified may be present but do not have to be. "Other substances" are the components not explicitly listed above. Furthermore, the proviso applies that the part by mass of alkenes in the feedstock mixture based on the total mass thereof is 1% by weight to 10% by weight, and that the feedstock mixture is provided in liquid form at a pressure between $0.1*10^5$ Pa and $6.0*10^5$ Pa.

It is important that the dehydrogenation temperature has not yet been reached in the presence of the first catalyst. Because of this, the feedstock mixture with the added hydrogen or the intermediate resulting therefrom is only brought to the dehydrogenation temperature gradually. Accordingly, the process is conducted in an apparatus having a heating zone and a reaction zone, wherein the first catalyst is arranged in the heating zone and the second catalyst is arranged in the reaction zone, and wherein the feedstock mixture or the intermediate is heated in the heating zone so that it enters the reaction zone at a temperature between 450° C. and 760° C. The contact with the first solid catalyst (i.e. the hydrogenation) therefore takes place in the heating zone at temperatures at which the dehydrogenation is not thermodynamically preferred. Typical hydrogenation temperatures are between 20° C. and 220° C. However, the hydrogenation temperature can be higher in the present case with the result that the feedstock mixture at reaction pressure of the dehydrogenation has to be evaporated. The hydrogenation temperature may also thus be between 220° C. and 450° C., at 350° C. for example. Critical for the delimitation between heating zone and reaction zone is thus the achievement of a thermodynamic state in which the equilibrium tips between hydrogenation and dehydrogenation.

The process is especially preferably conducted isobarically, which means that the prevailing pressure in the dehydrogenation also prevails in the hydrogenation and in the metered addition of hydrogen and in the evaporation of the feedstock mixture, which is already provided at the dehydrogenation pressure. Pressure losses due to flow/gas dynamics should therefore be disregarded.

A suitable apparatus for carrying out the process according to the invention comprises an intake for the feeding of a liquid feedstock mixture, which is under a pressure between $0.1*10^5$ Pa and $6.0*10^5$ Pa, an evaporator for evaporating the feedstock mixture by increasing the temperature thereof, a component for metering hydrogen into the evaporated feedstock mixture, a heating zone for heating the evaporated feedstock mixture or an intermediate resulting therefrom, means of heating the heating zone, a reaction zone for contacting the intermediate with a second solid catalyst in which the second solid catalyst is arranged and means of heating the reaction zone to a temperature between 450° C. and 760° C. In the heating section of the apparatus a first solid catalyst should be arranged and the entire apparatus should be designed for a pressure between $0.1*10^5$ Pa and $6.0*10^5$ Pa, such that the process can be conducted isobarically. Such an apparatus likewise forms part of the subject matter of the invention.

As already outlined above, the equilibrium between hydrogenation and dehydrogenation is shifted in the direction of dehydrogenation at higher temperature. If additional hydrogen is fed in however, the equilibrium is again shifted in the direction of hydrogenation. This also occurs at high temperatures (between 450° C. and 760° C.), at which the dehydrogenation is actually rather operated. It is also possible, therefore, to operate hydrogenation and dehydrogenation in one step over one catalyst under dehydrogenation conditions. For this reason, the addition of hydrogen according to the invention can even take place in the dehydrogenation reactor under dehydrogenation conditions, although it should be observed that the hydrogen content is limited such that it corresponds to the olefin content in the feed within very narrow limits (molar ratio of hydrogen to the alkenes present in the feedstock mixture is between 0.8:1 and 1.2:1), and therefore does not work against the equilibrium.

The single-stage process resulting therefrom has the controlled correlation of the hydrogen relative to the olefins in common with the two-stage process outlined above.

A corresponding process is therefore also a subject matter of the invention. It has the following steps:
  a) providing a liquid feedstock mixture at a pressure between $0.1*10^5$ Pa and $6.0*10^5$ Pa, wherein the feedstock mixture comprises alkanes having two to five carbon atoms and alkenes having two to five carbon atoms, and wherein the part by mass of alkenes in the feedstock mixture based on the total mass thereof is 1% by weight to 10% by weight;
  b) evaporating the feedstock mixture by increasing the temperature;
  c) adding hydrogen to the evaporated feedstock mixture such that the molar ratio of hydrogen to the alkenes present in the feedstock mixture is between 0.8:1 and 1.2:1;
  d) contacting the evaporated, hydrogen-containing feedstock mixture with a solid catalyst at a temperature between 450° C. and 760° C. and a pressure of $0.1*10^5$ Pa to $6.0*10^5$ Pa to obtain a product mixture, wherein the part by mass of the alkenes having two to five carbon atoms in the product mixture based on the total mass thereof is 30% by weight to 70% by weight.

A suitable system as solid catalyst is therefore used for the dehydrogenation which is catalytically effective both for the hydrogenation and the dehydrogenation, preferably a catalyst which comprises a support material and applied thereto at least one element selected from the group consisting of nickel, platinum and palladium. The one-stage process can incidentally also be regarded as a two-stage process in which the identical catalyst is used in both stages. Both variants therefore clearly have a common inventive concept.

The invention will now be explained in more detail by reference to a simplified process flow diagram.

FIGURE: Process flow diagram of the process according to the invention.

The feedstock mixture Feed is supplied in liquid form specifically at the pressure level of the subsequent dehydrogenation.

In an evaporator 1, the feedstock mixture is evaporated. This is accomplished by heating. In a component 2, hydrogen $H_2$ is metered into the evaporated feedstock mixture, specifically as precisely as possible the molar (stoichiometric) amount corresponding to the alkenes present in the feedstock mixture. The gaseous feedstock mixture enriched with hydrogen is then brought into contact with a first solid catalyst 3. Here, the alkenes present in the feedstock mixture Feed are hydrogenated with the hydrogen $H_2$ fed in to give the corresponding alkanes. Here, an intermediate Intermediate is obtained whose alkene proportion is now below 1% by weight.

Subsequently, the intermediate is now brought to a temperature level (450° C. to 760° C.) required for the dehydrogenation in a heat exchanger 4. It is also possible, however, to already preheat during the hydrogenation over the first catalyst 3 as long as the equilibrium reaction is not thereby shifted in the direction of dehydrogenation. It should also be noted that heat of reaction is already released by the exothermic hydrogenation which flows into the intermediate.

Since the temperature of the feedstock mixture or the intermediate resulting therefrom is already increased by the metered addition of hydrogen in component 2 until in the heat exchanger 4, this region is also interpreted as a heating zone.

The intermediate is now subjected to a dehydrogenation by contact over a second catalyst 5 such that a product mixture Product is formed, which comprises again a high proportion of alkenes (30 to 70% by weight). This is accomplished in a reaction zone of the process which follows the heating zone. The boundary between heating zone and reaction zone is at the point where the temperature is high such that dehydrogenation is favoured thermodynamically over hydrogenation. Since the dehydrogenation is endothermic, appropriate means to heat the reaction zone are required; a gas burner for example (not shown).

The first catalyst 3 and the second catalyst 5 may be different or identical. The heating zone and reaction zone may be separate apparatuses or be integrated. In an isobaric procedure, they are distinguished by the temperature.

LIST OF REFERENCE SYMBOLS

1: evaporator
2: component
3: first solid catalyst
4: heat exchanger
5: second solid catalyst
Feed: feedstock mixture
Intermediate: intermediate
Product: product mixture

The invention claimed is:
1. Process for preparing alkenes by dehydrogenation of alkanes having the following steps in a single stage or in two stage:
  a) providing a liquid feedstock mixture at a pressure between $0.1*10^5$ Pa and $6.0*10^5$ Pa, wherein the feedstock mixture comprises alkanes having two to five carbon atoms and alkenes having two to five carbon atoms, and wherein the part by mass of alkenes in the feedstock mixture based on the total mass thereof is 1% by weight to 10% by weight;

b) evaporating the feedstock mixture by increasing the temperature;

c) adding hydrogen to the evaporated feedstock mixture such that the molar ratio of hydrogen to the alkenes present in the feedstock mixture is between 0.8:1 and 1.2:1; and then d1) contacting the evaporated, hydrogen-containing feedstock mixture in a single stage with a solid catalyst for hydrogenation and dehydrogenation at a temperature between 450° C. and 760° C. and a pressure of $0.1*10^5$ Pa to $6.0*10^5$ Pa to obtain a product mixture, wherein the part by mass of the alkenes having two to five carbon atoms in the product mixture based on the total mass thereof is 30% by weight to 70% by weight; or d2) contacting the evaporated, hydrogen-containing feedstock mixture in two stages with a first solid catalyst and a pressure between $0.1*10^5$ Pa and $6*10^5$ Pa to obtain an intermediate, wherein the part by mass of the alkenes in the intermediate based on the total mass thereof is 0% by weight to 1% by weight and wherein the temperature of the intermediate is increased; and e) then contacting the intermediate with a second solid catalyst at a temperature between 450° C. and 760° C. and a pressure of $0.1*10$ Pa to $6.0*10^5$ Pa to obtain a product mixture, wherein the part by mass of the alkenes having two to five carbon atoms in the product mixture based on the total mass thereof is 30% by weight to 70% by weight.

2. Process according to claim 1, wherein the first solid catalyst and the second solid catalyst in the two stages are identical.

3. Process according to claim 2, wherein the catalysts comprise a support material and at least one element from groups 8, 9 and 10 of the Periodic Table of the Elements according to IUPAC convention.

4. Process according to claim 2, wherein the catalysts comprise a support material and at least tin and/or zinc.

5. Process according to claim 3, wherein the support material is silicon dioxide, aluminium oxide or a mixture of silicon dioxide and aluminium oxide.

6. Process according to claim 3, wherein the support material is an aluminate which has been formed from aluminium oxide and an alkaline earth metal.

7. Process according to claim 3, wherein the support material is hydrotalcite.

8. Process according to claim 1, wherein the first solid catalyst and the second solid catalyst are different.

9. Process according to claim 8, wherein the first solid catalyst comprises a support material and at least one element applied thereto selected from the group consisting of nickel, platinum and palladium.

10. Process according to claim 9, wherein the support material is silicon dioxide, aluminium oxide or a mixture of silicon dioxide and aluminium oxide.

11. Process according to claim 1, wherein the feedstock mixture has the following composition adding up to 100% by weight:

Propane: 0% by weight to 50% by weight;
Isobutane: 0% by weight to 100% by weight;
n-Butane: 0% by weight to 100% by weight;
Propene: 0% by weight to 10% by weight;
Isobutene: 0% by weight to 10% by weight;
n-Butene: 0% by weight to 100% by weight;
sum of other substances: 0% by weight to 5% by weight.

12. Process according to claim 1, wherein the process is conducted in an apparatus having a heating zone and a reaction zone, wherein the first solid catalyst is arranged in the heating zone and the second solid catalyst is arranged in the reaction one, and wherein the feedstock mixture is heated in the heating zone so that the intermediate enters the reaction zone at a temperature between 450° C. and 760° C.

13. Process according to claim 1, wherein the process is carried out isobarically.

* * * * *